US012758214B2

(12) United States Patent
Adams et al.

(10) Patent No.: US 12,758,214 B2
(45) Date of Patent: Oct. 13, 2026

(54) WIRING HARNESS FOR SMART STAPLER WITH MULTI AXIS ARTICULATION

(71) Applicant: Cilag GmbH International, Zug (CH)

(72) Inventors: Shane R. Adams, Lebanon, OH (US); Matthew D. Cowperthwait, Cincinnati, OH (US); Adam D. Hensel, Gahanna, OH (US); Frederick E. Shelton, IV, Hillsboro, OH (US); Sarah A. Worthington, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 212 days.

(21) Appl. No.: 18/379,777

(22) Filed: Oct. 13, 2023

(65) Prior Publication Data

US 2025/0120693 A1 Apr. 17, 2025

(51) Int. Cl.
*A61B 17/068* (2006.01)
*A61B 17/00* (2006.01)

(52) U.S. Cl.
CPC .... *A61B 17/068* (2013.01); *A61B 2017/0069* (2013.01)

(58) Field of Classification Search
CPC .. A61B 2017/00017; A61B 2017/0069; A61B 2017/2927; A61B 17/068; A61B 17/07207
USPC ........................................................ 227/175.1
See application file for complete search history.

(56) References Cited

U.S. PATENT DOCUMENTS

| | | | | |
|---|---|---|---|---|
| 7,980,443 | B2 | 7/2011 | Scheib et al. | |
| 8,393,514 | B2 | 3/2013 | Shelton, IV et al. | |
| 8,561,870 | B2 | 10/2013 | Baxter, III et al. | |
| 8,733,613 | B2 | 5/2014 | Huitema et al. | |
| 8,991,678 | B2 | 3/2015 | Wellman et al. | |
| 9,072,535 | B2 | 7/2015 | Shelton, IV et al. | |
| 9,629,629 | B2 | 4/2017 | Leimbach et al. | |
| 2019/0201023 | A1 * | 7/2019 | Shelton, IV | A61B 18/14 |
| 2021/0085325 | A1 | 3/2021 | Shelton, IV et al. | |
| 2023/0133811 | A1 * | 5/2023 | Huang | A61B 17/07207 227/176.1 |

* cited by examiner

*Primary Examiner* — Eronica Martin
*Assistant Examiner* — Mary C Hibbert-Copeland
(74) *Attorney, Agent, or Firm* — Lempia Summerfield Katz LLC

(57) ABSTRACT

A surgical instrument is provided. The surgical instrument comprises a shaft, a multi-axis articulation joint assembly defining a cavity therein, and a wiring assembly disposed within the shaft and the multi-axis articulation joint assembly. The multi-axis articulation joint assembly comprises a first articulation joint and a second articulation joint. The wiring assembly comprises a wiring harness having a thickness and a width greater than the thickness, and a preset twist. An articulation joint assembly is also provided.

20 Claims, 11 Drawing Sheets

WIRING HARNESS FOR SMART STAPLER WITH MULTI AXIS ARTICULATION

BACKGROUND

The present invention relates to surgical instruments and, in various arrangements, to surgical stapling and cutting instruments and staple cartridges for use therewith that are designed to staple and cut tissue.

SUMMARY

The following summary is provided to facilitate an understanding of some of the innovative features unique to the aspects disclosed herein and is not intended to be a full description. A full appreciation of the disclosure herein can be gained by taking the entire specification, claims, and abstract as a whole.

A surgical instrument is disclosed. The surgical instrument includes a shaft, a multi-axis articulation joint assembly defining a cavity therein, and a wiring assembly disposed within the shaft and the multi-axis articulation joint assembly. The multi-axis articulation joint assembly includes a proximal end, a distal end, a first articulation joint disposed between the proximal end and the distal end and a second articulation joint distal to the first articulation joint. The first articulation joint is configured to move in a first articulation plane, and the second articulation joint is configured to move in a second articulation plane transverse to the first articulation plane. The wiring assembly includes a wiring harness extending through the cavity of the articulation joint assembly. The wiring harness has a thickness and a width greater than the thickness. The wiring harness includes a proximal flat portion that spans the first articulation joint in a non-articulated state, a distal flat portion that spans the second articulation joint in the non-articulated state and a preset twist between the proximal flat portion and the distal flat portion. The preset twist biases the distal flat portion into a different orientation than the proximal flat portion, in the non-articulated state.

An articulation joint assembly for a surgical instrument is disclosed. The articulation joint assembly includes a multi-axis articulation joint assembly defining a cavity therein and a wiring assembly disposed within the multi-axis articulation joint assembly. The multi-axis articulation joint assembly includes a proximal end, a distal end, a first articulation joint disposed between the proximal end and the distal end and a second articulation joint distal to the first articulation joint. The first articulation joint is configured to move in a first articulation plane, and the second articulation joint is configured to move in a second articulation plane transverse to the first articulation plane. The wiring assembly includes a wiring harness extending through the cavity of the articulation joint assembly. The wiring harness has a thickness and a width greater than the thickness. The wiring harness includes a proximal flat portion that spans the first articulation joint in a non-articulated state, a distal flat portion that spans the second articulation joint in the non-articulated state and a preset twist between the proximal flat portion and the distal flat portion. The preset twist biases the distal flat portion into a different orientation than the proximal flat portion, in the non-articulated state.

BRIEF DESCRIPTION OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views.

DETAILED DESCRIPTION

Figure 1:
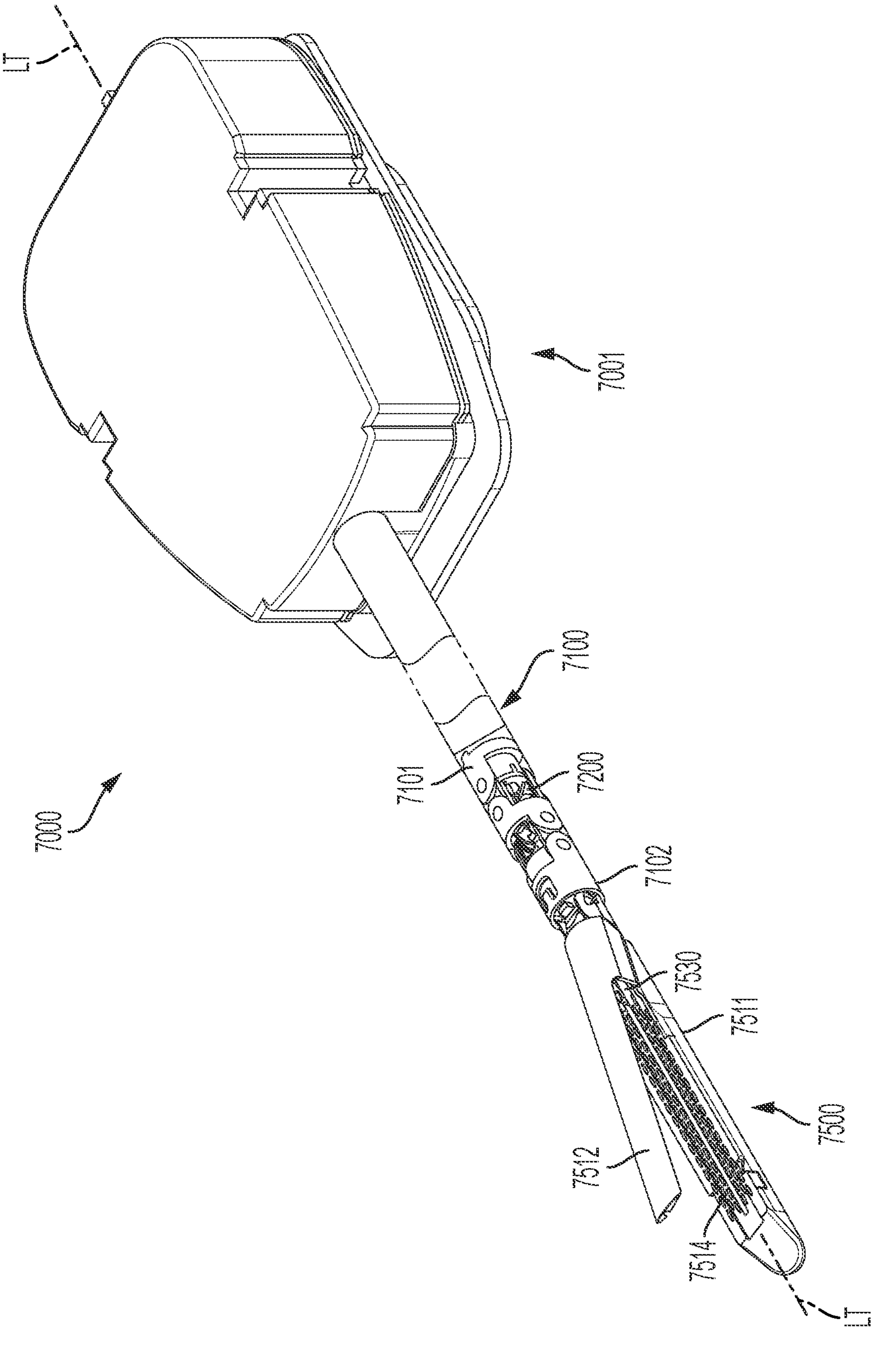
FIG. 1 illustrates a perspective view of a surgical instrument, in accordance with the present disclosure.

Applicant of the present application owns the following U.S. patent applications that were filed on even date herewith and which are each herein incorporated by reference in their respective entireties:

- U.S. patent application Ser. No. 18/379,759, titled METHOD OF OPERATING A SURGICAL STAPLING INSTRUMENT;
- U.S. patent application Ser. No. 18,379,762, titled SURGICAL STAPLING SYSTEMS WITH ADAPTIVE STAPLE FIRING ALGORITHMS;
- U.S. patent application Ser. No. 18/379,763, titled LEARNED TRIGGERS FOR ADAPTIVE CONTROL OF SURGICAL STAPLING SYSTEMS;
- U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;
- U.S. patent application Ser. No. 18/379,768, titled PROPORTIONATE BALANCING OF THE FUNCTION IMPACT MAGNITUDE OF BATTERY OUTPUT TO PEAK MOTOR CURRENT;
- U.S. patent application Ser. No. 18/379,771, titled MOTOR OPTIMIZATION BY MINIMIZATION OF PARASITIC LOSSES AND TUNING MOTOR DRIVE CONFIGURATION;
- U.S. patent application Ser. No. 18/379,773, titled APPARATUS AND METHOD TO REDUCE PARASITIC LOSSES OF THE ELECTRICAL SYSTEM OF A SURGICAL INSTRUMENT;

U.S. patent application Ser. No. 18,379,776, titled SURGICAL TOOL WITH RELAXED FLEX CIRCUIT ARTICULATION;

U.S. patent application Ser. No. 18/379,781, titled SURGICAL SYSTEM WITH WIRELESS ARRAY FOR POWER AND DATA TRANSFER; and U.S. patent application Ser. No. 18/379,784, titled SURGICAL STAPLE CARTRIDGE COMPRISING REPLACEABLE ELECTRONICS PACKAGE;

Applicant of the present application owns the following U.S. patent applications that were filed on even date herewith and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,796, titled INTEGRAL CARTRIDGE STIFFENING FEATURES TO REDUCE CARTRIDGE DEFLECTION;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,803, titled PANLESS STAPLE CARTRIDGE ASSEMBLY COMPRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;

U.S. patent application Ser. No. 18/379,831, titled STAPLE CARTRIDGES COMPRISING TRACE RETENTION FEATURES; and U.S. patent application Ser. No. 18/379,832, titled STAPLE CARTRIDGES COMPRISING STAPLE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various methods, instruments, and systems are provided for performing surgical procedures. Various surgical systems disclosed herein include working portions that can be inserted into a body in any way, such as through a natural orifice, through an incision or puncture hole formed in tissue, etc. The working portions or end effector portions can be inserted directly into a patient's body or can be inserted through an access device that has a working channel. As the present Detailed Description proceeds, it will be understood that the various unique and novel arrangements of the various forms of surgical systems disclosed herein may be effectively employed in connection with robotically-controlled surgical systems and/or hand-held surgical systems. Various robotic systems, instruments, components and methods are disclosed in U.S. patent application Ser. No. 13/118,241, entitled SURGICAL STAPLING INSTRUMENTS WITH ROTATABLE STAPLE DEPLOYMENT ARRANGEMENTS, which is incorporated by reference herein in its entirety.

FIG. 1 provides a perspective view of a surgical instrument 7000, in accordance with the present disclosure. The surgical instrument 7000 includes a shaft 7100 and a multi-axis articulation joint assembly 7200. The shaft 7100 defines a longitudinal axis LT. In instances where the surgical instrument 7000 is robotically manipulated, the shaft 7100 can be coupled to a robotic arm or an intermediary mount for a robotic arm, such as, for example, a tool mounting portion 7001, as depicted in FIG. 1. In other instances where the surgical instrument is handheld, the shaft 7100 is coupled to a handle, for example. The shaft 7100 further includes a distal shaft portion 7102. The surgical instrument may further comprise an end effector 7500 coupled to the distal shaft portion 7102 and/or the multi-axis articulation joint assembly 7200.

Figure 2:
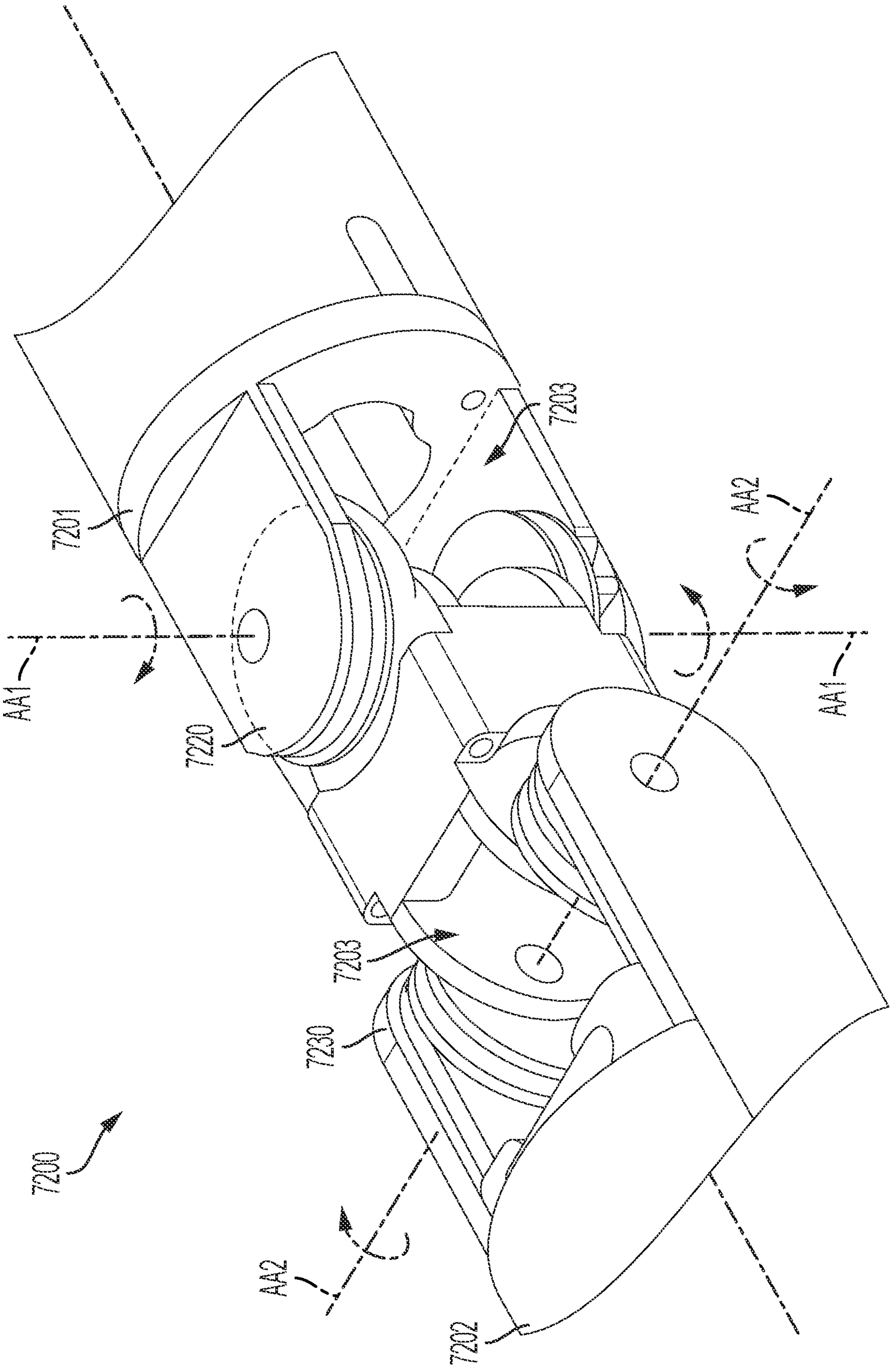
FIG. 2 illustrates an articulation joint assembly, in accordance with the present disclosure.

Further to the above, the multi-axis articulation joint assembly 7200 extends between a proximal shaft portion 7101 and the distal shaft portion 7102. As illustrated in FIG. 2, the multi-axis articulation joint assembly 7200 includes a proximal end 7201, a distal end 7202, and first and second articulation joints 7220, 7230. The multi-axis articulation joint assembly includes a cavity 7203 extending between the proximal end 7201 and the distal end 7202.

In accordance with the present disclosure, when the multi-axis articulation assembly 7200 is in a non-articulated state, the first articulation joint 7220 and the second articulation joint 7230 can be longitudinally separated by a longitudinal distance D and the multi-axis articulation joint assembly 7200 is aligned with the longitudinal axis LT of the surgical instrument 7000. Additional details are described in U.S. patent application Ser. No. 17/032,279, entitled SURGICAL STAPLING INSTRUMENTS WITH ROTATABLE STAPLE DEPLOYMENT ARRANGEMENTS, Sep. 25, 2020, which is hereby incorporated by reference herein in its entirety.

Figure 3:
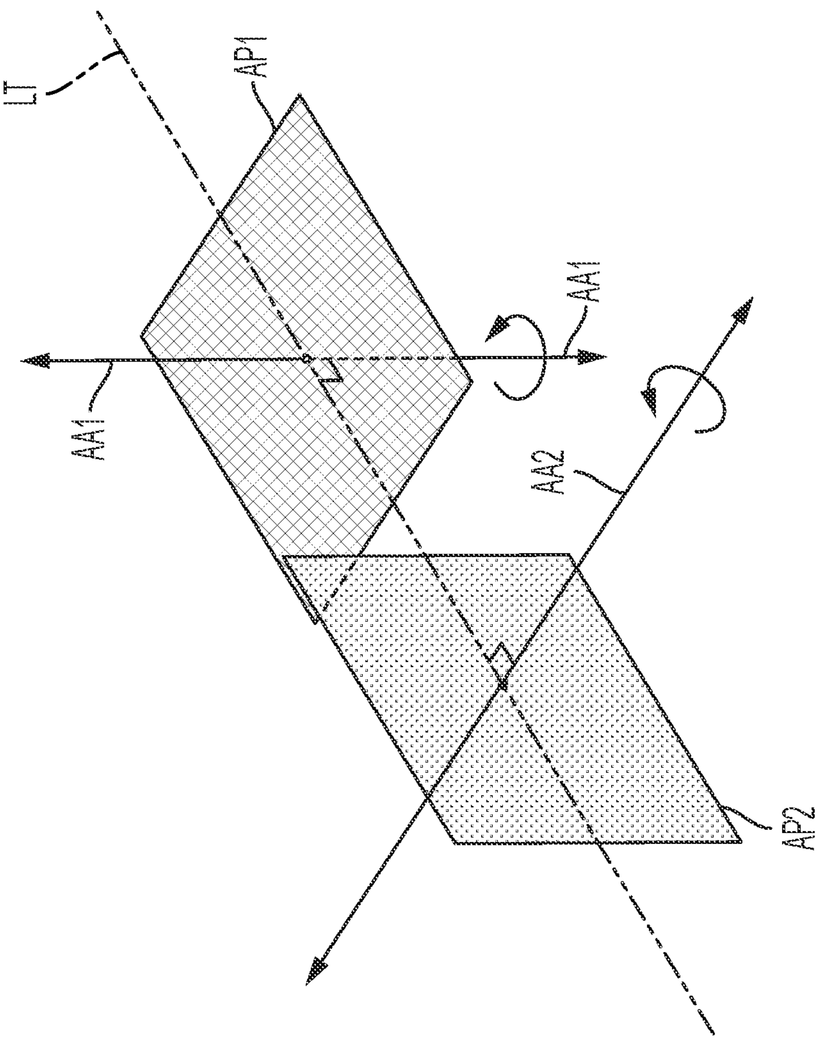
FIG. 3 illustrates articulation axes and articulation planes of the articulation joint assembly of FIG. 2.

Further to the above, the multi-axis articulation joint assembly 7200 is able to transition from a non-articulated state, as illustrated in FIGS. 1-3, to an articulated state by moving the first articulation joint 7220 and/or the second articulation joint 7230 in articulation planes AP1 and AP2 about articulation axes AA1 and AA2, respectively. As used in the present disclosure in relation to a particular articulation joint in a non-articulated state, an articulation plane is defined as a plane that is perpendicular to the articulation axis of the articulation joint, such that both planes longitudinally extend with the longitudinal axis LT. For example, FIG. 3 provides a geometric representation of the spatial relationships between articulation axes AA1/AA2, articulation planes AP1/AP2, and the longitudinal axis LT. Although FIG. 3 depicts articulation axes AA1 and AA2 as intersecting longitudinal axis LT within respective articulation planes AP1 and AP2, it is envisioned that the articulation axes and/or articulation planes may not be aligned with one another in other implementations with respect to the longitudinal axis LT, such as, for example, with offset articulation joints.

Still referring to FIGS. 1-3, the multi-axis articulation joint assembly 7200 is configured to articulate in multiple planes. In accordance with the present disclosure, the first articulation joint 7220 and the second articulation joint 7230 can be oriented such that the articulation planes AP1 and AP2 are transverse with one another. Said in another way, the articulation joints 7220 and 7230 can be rotationally offset from each other with respect to the longitudinal axis LT. For example, as best illustrated in FIGS. 2-3, the articulation planes AP1 and AP2 are perpendicularly offset from one another in the non-articulated state.

Now referring back to FIG. 1, the distal shaft portion 7102 can be coupled to an end effector 7500 including a first jaw 7511 and a second jaw 7512 movable relative to the first jaw 7511 to transition the end effector 7500 from an open configuration, as illustrated in FIG. 1, to a closed configuration to grasp tissue between the first jaw 7511 and the second jaw 7512. In the illustrated example, the first jaw 7511 includes a staple cartridge 7514 including staples deformable against staple forming pockets of an anvil in the second jaw 7512. In accordance with the present disclosure, the first jaw 7511 and the second 7512 may be equipped with electrodes configured to deliver therapeutic and/or non-therapeutic energy to the grasped tissue. Additionally, a firing beam 7530 for driving a sequential deployment of staples from the staple cartridge 7514 and for cutting the stapled tissue may be coupled to an internal firing shaft extending along the longitudinal axis LT within the surgical instrument 7000. Additional details are described in U.S. patent application Ser. No. 14/200,111, entitled CONTROL SYSTEMS FOR SURGICAL INSTRUMENTS, filed Mar. 7, 2014, which issued on Apr. 25, 2017 as U.S. Pat. No. 9,629,629, which is hereby incorporated by reference herein in its entirety.

Figure 4:
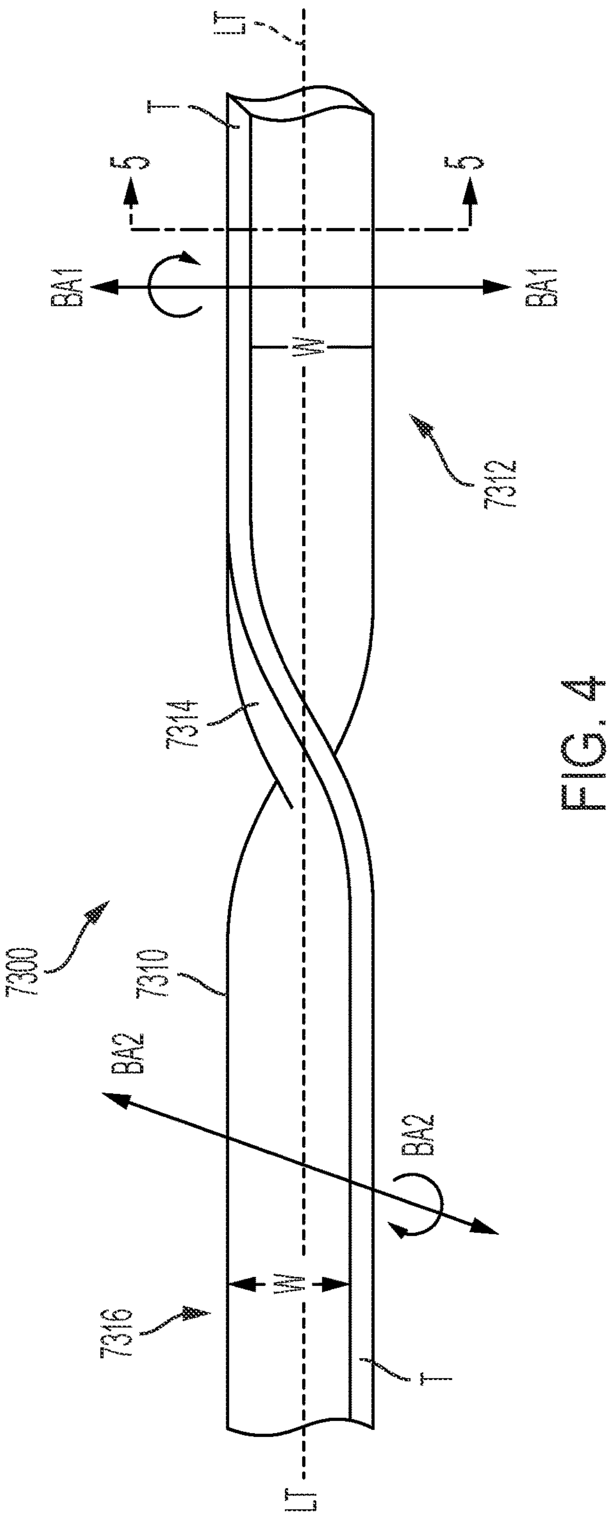
FIG. 4 illustrates a perspective view of a wiring harness in a non-articulated state, in accordance with the present disclosure.
Figure 5:
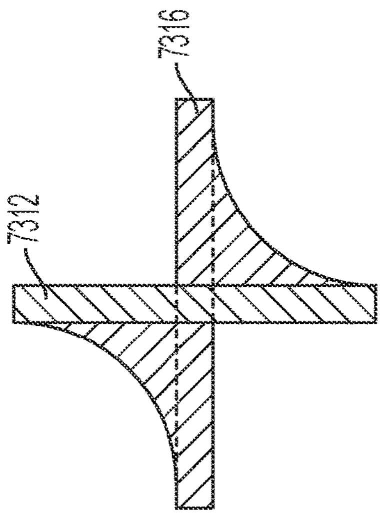
FIG. 5 illustrates an axial view of the of the wiring harness of FIG. 4.
Figure 6:
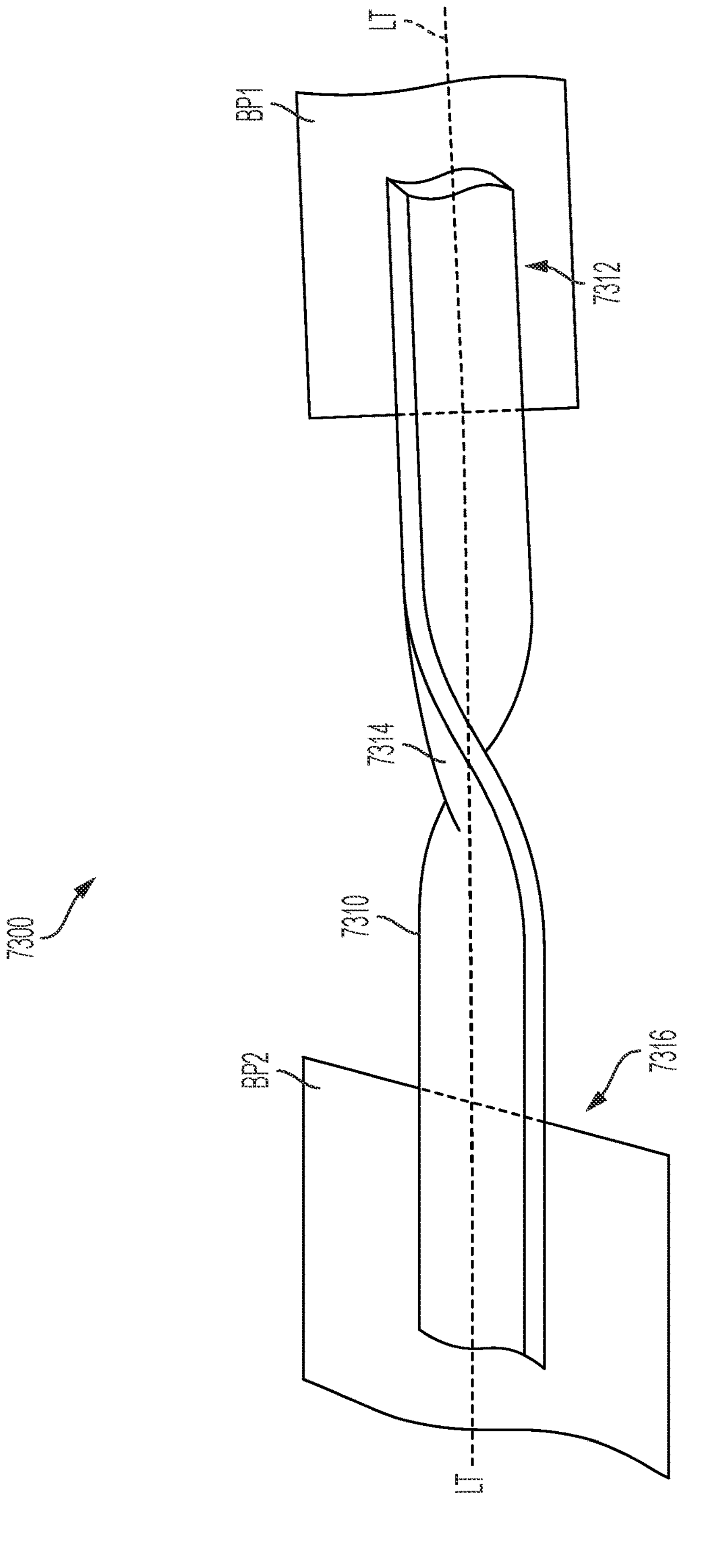
FIG. 6 illustrates bending planes of the wiring harness of FIG. 4.

The surgical instrument 7000 further includes a wiring assembly 7300 disposed within the shaft 7100 and the multi-axis articulation joint assembly 7200. The wiring assembly 7300 includes a wiring harness extending through the cavity 7210 of the multi-axis articulation joint assembly 7200 that transmits at least one of data or power through the multi-axis articulation joint assembly 7200 to a further distal component, such as an end effector 7500, from a power source or a data source proximal to the multi-axis articulation joint assembly 7200. In accordance with the present disclosure, the wiring assembly 7300 can transmit power to the end effector 7500 for powering a chip in the staple cartridge 7514, for example. Additionally, or alternatively, the wiring assembly 7300 may define a communication pathway between the chip and a processor of the surgical instrument 7000 positioned proximal to the multi-axis articulation joint assembly 7200. Portions of the wiring assembly 7300, such as a wiring harness 7310, are able to transition between a non-articulated state, such as illustrated in FIGS. 4-6, and articulated states, such as the articulated state illustrated in FIG. 7-8, as described in greater detail below.

Routing a wiring harness through a multi-axis articulation joint requires some manner of accommodation for transitioning between various rotationally offset articulation planes along the length of the multi-axis articulation joint. One accommodation is to incorporate reinforcements, such as strain reliefs or wiring harness junctions, into sections of the wiring harness where any significant amount of flexing and/or bending during an articulation is anticipated. However, the reinforcements themselves may have a limited number of activation cycles before exhibiting a decline in elasticity, interference due to debris, and/or fatigue of copper strands within the wiring harness.

Additionally, there is generally limited space allowed for a wiring harness, and any required movement thereof, within a cavity of a multi-axis articulation joint. Therefore, the use of any reinforcements therein must be balanced with the number of desired conductors and/or geometry thereof to avoid limiting a range of articulation and/or increasing the footprint of the articulation joint. While round cabling can bend in multiple directions, round cables are typically not space efficient and can be limited in allowable bend radius, especially in situations where a multiconductor harness is desirable.

Furthermore, flat wiring harnesses can contain many conductors placed side-by-side spanning the width of the flat wiring harness. This arrangement can be resilient to repeated flexing and/or bending while providing better space efficiency than round cabling. However, flat wiring harnesses are generally limited to flexing about a single linear axis. For example, a flat wiring harness may be resilient to repetitive bends when a thickness thereof is subjected to deformations or bends about a single bend axis parallel to, or extending along, a width of the flat wiring harness with a bend radius extending along the thickness. Said another way, the plane along which a width of the flat wiring harness extends is generally transversely oriented with respect to a plane of rotation. Implementing a flat wiring harness within a multi-axis articulation joint can require multiple flat sections adjoined and reinforced by connector sections should multiple bending planes be required, thereby increasing the overall footprint of the wiring harness. Thus, standard implementations of wiring harnesses through a multi-axis articulation may result in a limited articulation range and/or electrical communication through the wiring harness, and/or a larger articulation joint footprint, each of which is undesirable.

The present disclosure presents solutions that avoid the forgoing challenges. In accordance with the present disclosure, as illustrated in FIG. 4, the wiring assembly 7300 can include a wiring harness 7310 having a cross-sectional profile defined by a thickness T and a width W greater than the thickness T. As best illustrated in FIG. 6, the wiring harness 7310 includes a proximal flat portion 7312 corresponding to a first bending plane BP1 and a distal flat portion 7316 corresponding to a second bending plane BP2, with the bending planes BP1, BP2 transecting the thickness of wiring harness 7310 at the proximal and distal flat portions, respectively. The wiring harness 7300 also includes a preset twist 7314 spanning a longitudinal distance between the proximal flat portion 7312 and the distal flat portion 7316. The preset twist 7314 biases the distal flat portion 7316 into a different orientation than the proximal flat portion 7312. As discussed in greater detail below, the different orientations of the flat portions 7312 and 7316 facilitate a full range of articulation without the need for any auxiliary reinforcement sections.

Figure 8:
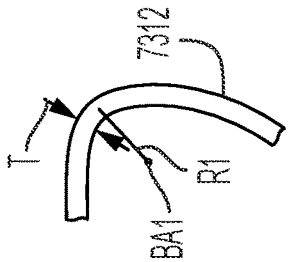
FIG. 8 illustrates a partial plan view of the wiring harness perspective view of the wiring harness of FIG. 7.
Figure 7:
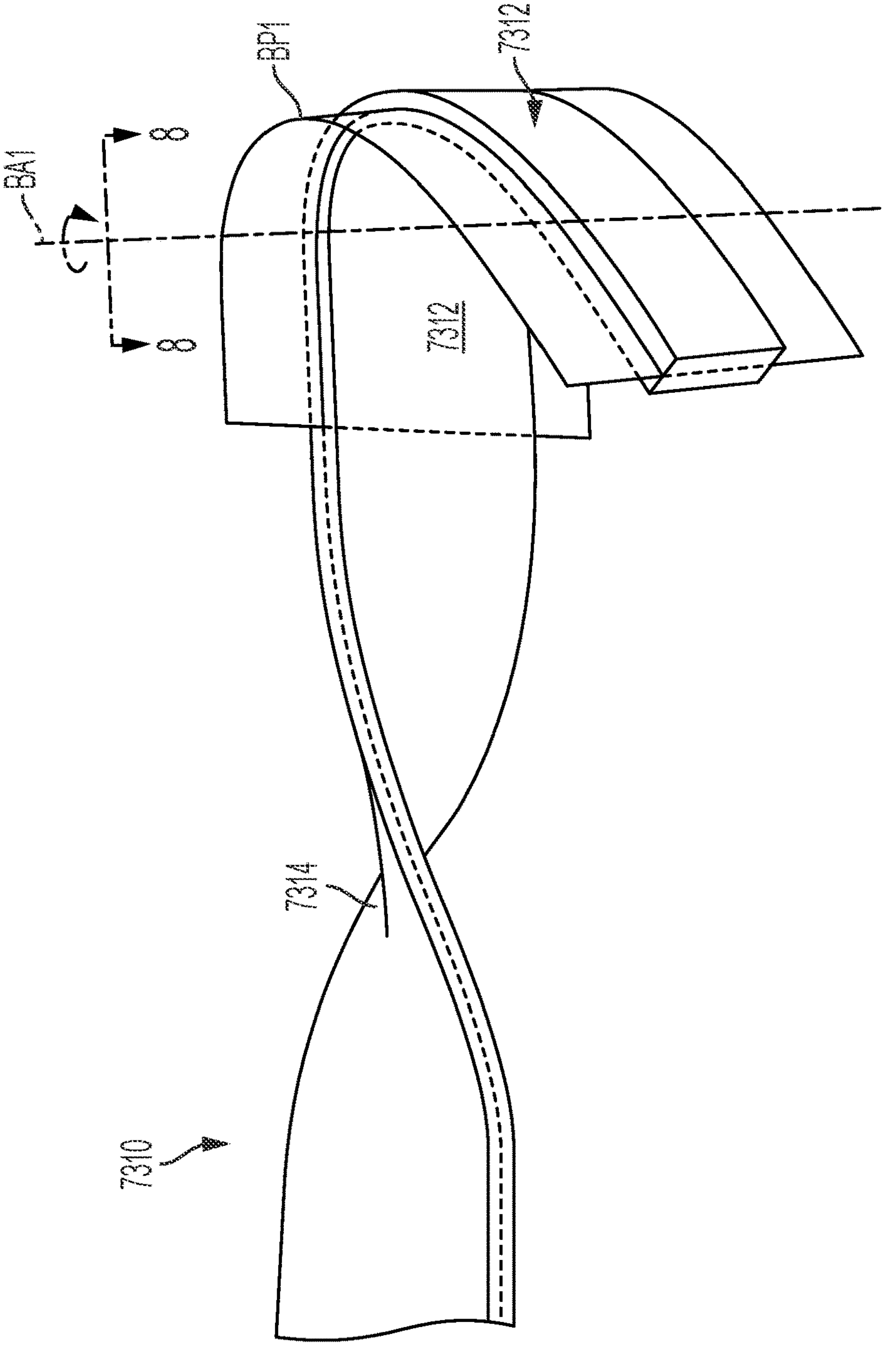
FIG. 7 illustrates a perspective view of a wiring harness in an articulated state, in accordance with the present disclosure.

Now referring to FIGS. 4-8, in the non-articulated state, the proximal flat portion 7312 spans the first articulation joint 7220 and the distal flat portion 7316 spans the second articulation joint 7230 such that the wiring harness 7310 may bend along with the first and/or second articulation joints 7220, 7230 to an articulated state, such as the articulated state illustrated in FIGS. 7-8 where the proximal flat portion 7212 is following a rotated first articulation. As best illustrated in FIGS. 6-7, the proximal flat portion 7312 comprises a first orientation in the non-articulated state such that a first bend radius R1 of the proximal flat portion 7312 in the articulated state extends through the thickness of wiring harness at the proximal flat portion 7312. Likewise, the distal flat portion 7316 comprises a second orientation in the non-articulated state such that a second bend radius R2 of the distal flat portion 7316 in the articulated state extends through the thickness of the wiring harness at the distal flat portion 7316. In accordance with the present disclosure, the first bend radius R1 and the second bend radius R2 may be greater than, or equal to, about 2× the thickness of the respective proximal flat portion and the distal flat portion throughout a full range of articulation of the articulation joints to minimize, or eliminate, overstressing the wiring harness 7310. Thus, the wiring harness 7310 remains unstretched during the full range of articulation such that the positioning of the preset twist 7314 with respect to the proximal end 7201 and/or the distal end 7202 remains the unchanged. Accordingly, this configuration of the wiring harness 7310 maintains the orientation and alignment of the flat portions 7312 and 7316 with the articulation joints 7220 and 7230, thereby minimizing, or eliminating, the need to supplement the harness with reinforcing and/or strain relief sections.

Further to the above, the proximal flat portion 7312 is associated with a first bending plane BP1 and the distal flat portion 7316 is associated with a second bending plane BP2, where the width of the wiring harness at each portion extends along the corresponding bending plane. In the non-articulated state, the bending planes BP1, BP2 intersect respective articulation planes AP1/AP2 and thus, are transversely oriented to their respective articulation planes and to one another. In accordance with the present disclosure, the bending planes BP1/BP2 may intersect the articulation planes AP1/AP2 such that their normal vectors intersect each other perpendicularly. Furthermore, each of the bending planes may curve or deform with the wiring harness, such as during an articulation, as illustrated in FIG. 7.

Further to the above, the preset twist 7314 is configured to accommodate the multiplanar articulations without incorporating additional reinforcements into the wiring harness 7310. In accordance with the present disclosure, the preset twist 7314 can define an angle that corresponds to the rotational offset between the first and second articulation joints 7220 and 7230. In the context of the present disclosure, the angle of the preset twist 7314 can be defined by the rotational offset between the flat portions 7312, 7316 adjoining the preset twist 7314 when viewed from the proximal end 7201 or distal end 7202 in the non-articulated state.

Additionally, the preset twist 7314 is maintained, or partially maintained, throughout a full range of motion of the articulation joint assembly, thereby preserving the relative planar orientations between the flat sections 7312, 7316 and respective articulation planes AP1, AP2 in the non-articulated state. The preset twist 7314 can be integrated into the wiring harness 7310 prior to assembling the surgical instrument. Additionally, the substrate of the wiring harness 7310 may comprise a tough yet flexible polymeric base material, such as, for example, a polyimide-based material, and may be molded to position the preset twist 7314 between the first and second articulation joints 7220/7230 upon routing the wiring harness 7310 through the surgical instrument 7000. Any layers of the wiring harness 7310 may also comprise the polymeric base material and/or another suitable flexible base material having desirable electrical properties. Thus, the wiring harness 7310 does not have to be rearranged and/or stretched from a resting state to provide the preset twist 7314, thereby avoiding any differences in space requirements for the wiring harness 7310 between non-articulated and articulated states. Additionally, the preset twist 7314 obviates the need for a separate biasing member to maintain the orientations of the adjoining flat portions 7312, 7316, thereby minimizing the number of additional components within the multi-axis articulation assembly and issues associated therewith.

In accordance with the present disclosure, the preset twist 7314 can be a permanent twist preformed prior to assembly with the surgical instrument 7000. Further, in accordance with the present disclosure, the preset twist 7314 can be formed by heating the polymeric base material of the wiring harness 7310, twisting the wiring harness to form the preset twist 7314, then allowing the polymeric base material to cool down. Additionally, more than one preset twist 7314 can be defined in the wiring harness 7310. In accordance with the present disclosure, one or more preset bends may be defined in the wiring harness 7310 in addition to, or instead of, the preset twist 7314. The preset twist 7314 can be formed by twisting the wiring harness 7310 to a twist angle that corresponds to a desired angle between articulation planes AP1, AP2, for example.

Figure 9A:
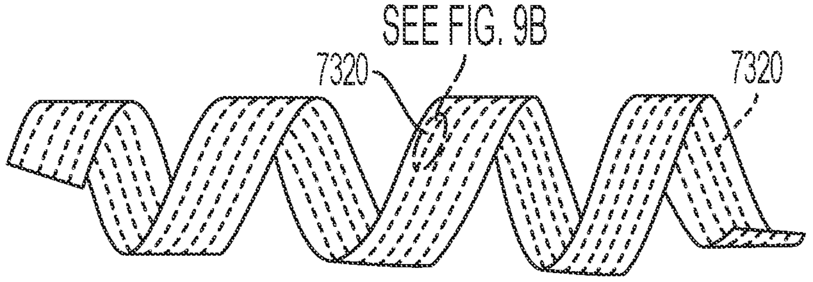
FIG. 9A illustrates conductive elements of a wiring harness, in accordance with the present disclosure.
Figure 9B:
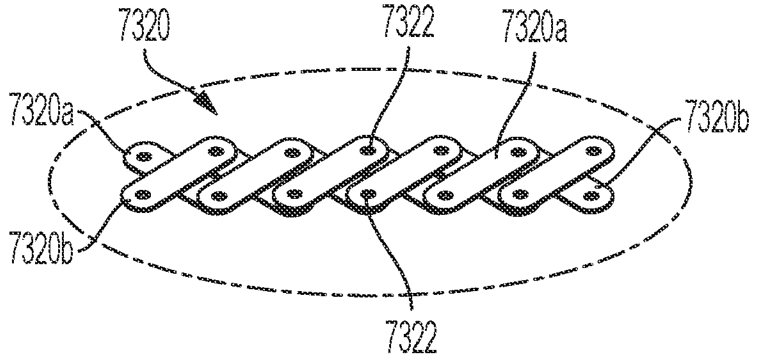
FIG. 9B illustrates an exploded view of conductive elements of FIG. 9A.

FIGS. 9A-9B illustrate conductive paths 7320 of the wiring harness 7310, in accordance with the present disclosure. The wiring harness 7310 may include conductive paths 7320 embedded within a substrate for transmitting power and/or data. The wiring harness 7310 may comprise multiple layers with at least some of the conductive paths 7320 positioned in closely arranged pairs. For example, as best illustrated in FIG. 9B, a conductive path 7320 can comprise a first group of conductive elements 7320*a* and a second group of conductive elements 7320*b* with each group providing separate portions of a conductive path, such as a supply and a return portion. Adjacent conductive elements of a particular group alternate between a top wiring harness layer and a bottom wiring harness layer while being connected with intermediate connectors 7322, each of which span the top and bottom wiring harness layers. In accordance with the present disclosure, the intermediate connectors 7322 can comprise a plated through-hole, a pin, and/or a conductive polymer. The wiring harness 7310 may further include an insulative intermediate layer between a bottom conductive element 7320*a* and an overlapping top conductive element 7320*b* to prevent electrical contact between the two groups and/or shielding layers sandwiched around conductive elements 7320*a*, 7320*b*. This arrangement can provide benefits such as electromagnetic interference rejection and/or common-mode noise rejection, which are traditionally associated with twisted pair wiring and/or shielded cabling, without using round conductors. Thus, the wiring harness 7310 and conductive elements 7320*a*, 7320*b* therein can provide advantages, such as increased space efficiency and flexibility, over other harnesses employing round conductor.

In accordance with the present disclosure, a proximal portion 7340 of the wiring assembly 7300 is housed in a retainer 7103 nested within the shaft 7100. The proximal portion 7340 is similar in many aspects to other wiring harnesses described elsewhere in the present disclosure. Thus, the proximal portion 7340 can have a cross-sectional profile defined by a thickness and a width greater than the thickness, and multiple conductive paths embedded in a tough and resilient polymeric base layer. Additionally, the proximal portion 7340 is in electrical communication with the wiring harness 7310 and/or physically joined therewith. Further, in accordance with the present disclosure, the proximal portion 7340 and the wiring harness 7310 can be routed through the surgical instrument 7000 as a single assembly.

Figure 10:
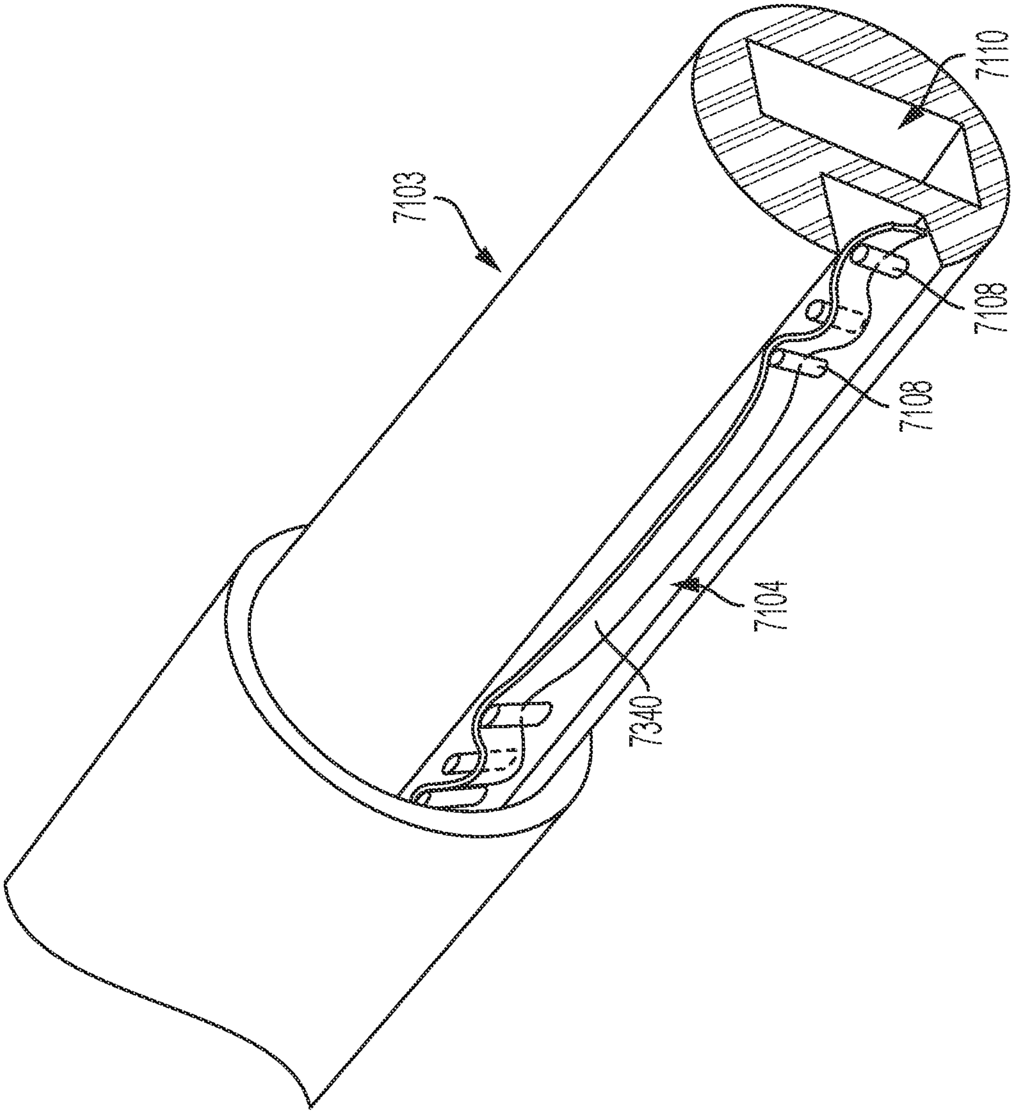
FIG. 10 illustrates a perspective view of a retainer, in accordance with the present disclosure.
Figure 11:
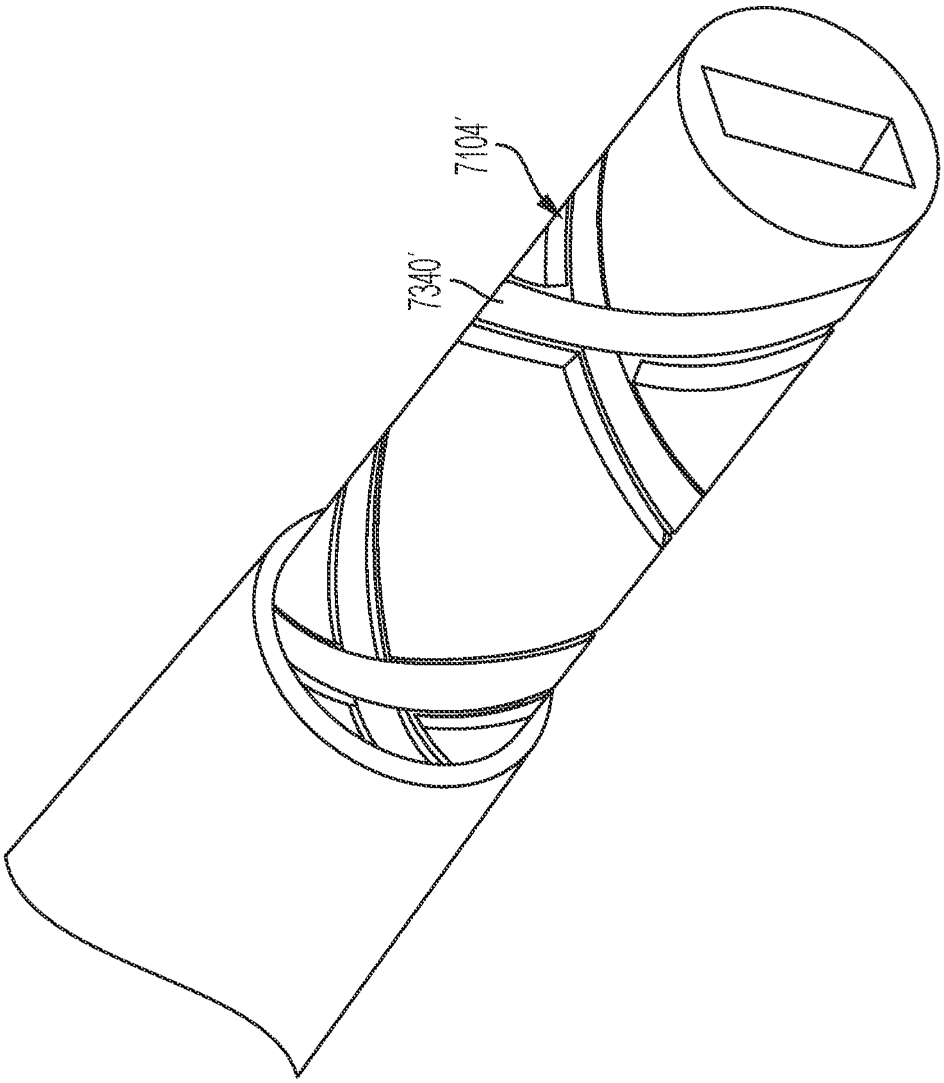
FIG. 11 illustrates a perspective view of a retainer, in accordance with the present disclosure.
Figure 12:
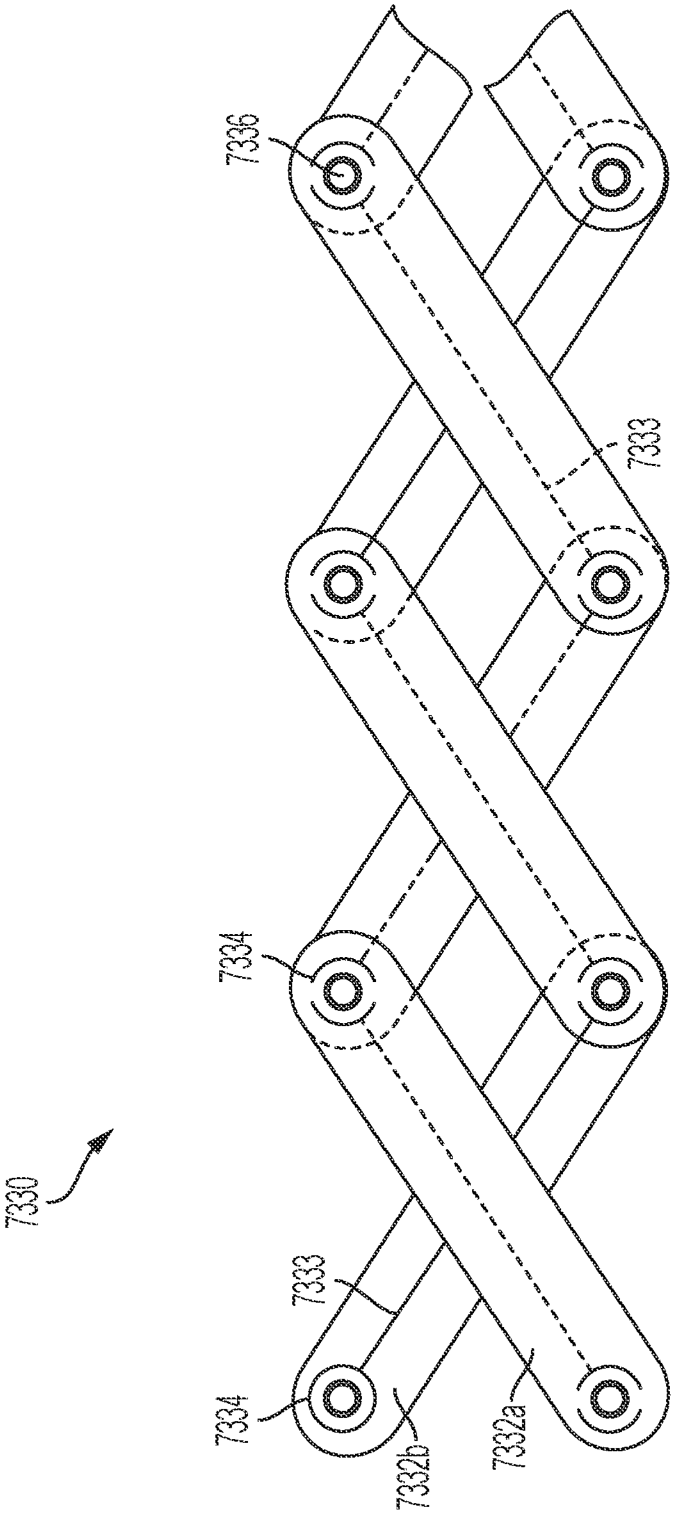
FIG. 12 illustrates scissoring portions of a wiring assembly, in accordance with the present disclosure.

Now referring to FIG. 10, a perspective view of a retainer 7103 is provided, in accordance with the present disclosure. The retainer 7103 is nested within the shaft 7100 and comprises a plastic material. A channel 7104 is defined in an outer surface 7106 of the retainer thereof. Additionally, the channel 7104 can be configured to guide the proximal portion 7340 of the wiring assembly 7300 from a power and/or communication source proximal to the shaft 7100 toward the multi-axis articulation joint assembly 7200. Further, in accordance with the present disclosure, the channel 7104 can span an axial length of the retainer 7103. Additionally, or alternatively, one or more helical channels 7104' can be defined in the outer surface of the retainer as illustrated in FIG. 12. The retainer 7103 can further comprise an inner channel 7110 to accommodate a longitudinally extending component such as a firing shaft.

The channel 7104 may be supplemented by guiding posts 7108 to maintain an orientation of the portion of the wiring assembly 7300 therein. The guiding posts 7108 may be molded out of the same material as the retainer 7103 and spaced such that they do not impart any friction on the proximal portion 7340 of the wiring assembly or impede any movements thereof which may occur during operation of the surgical instrument 7000. The guiding posts 7108 may be longitudinally offset from each other to facilitate routing the proximal portion 7340 of the wiring assembly therethrough without introducing an amount of curvature into the proximal portion 7340 which would induce binding in the longitudinal direction. Additionally, or alternatively, slots can be molded into the retainer 7103 for routing the wiring assembly therethrough.

Figure 13:
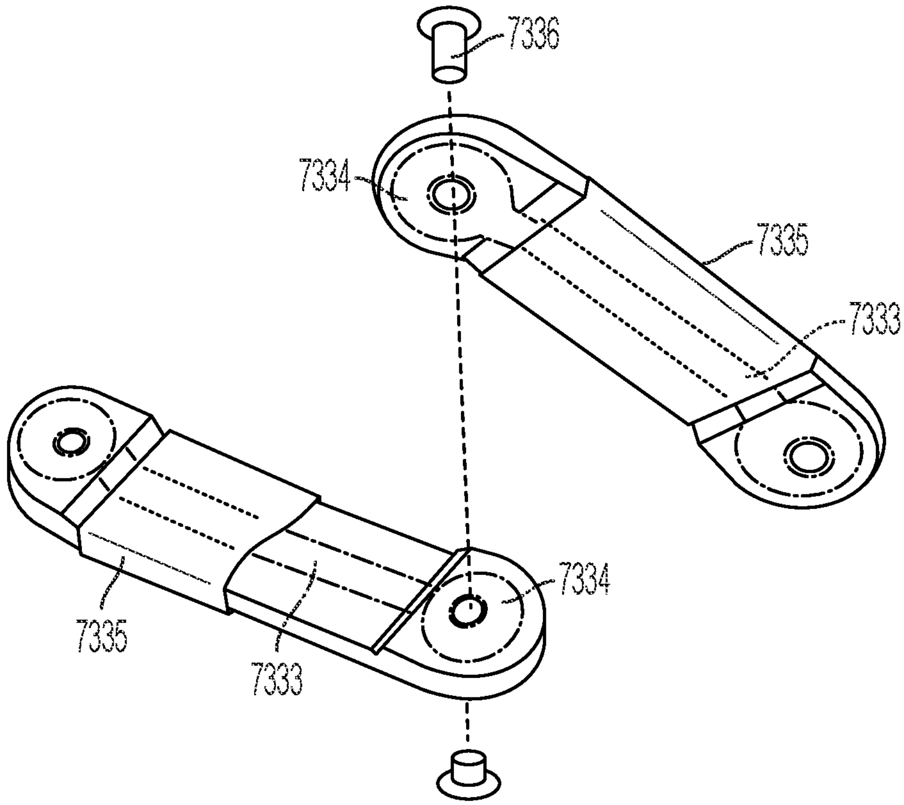
FIG. 13 illustrates linkages of the scissoring portions of FIG. 12.

Further to the above, the wiring assembly 7300 may include scissoring portions to facilitate longitudinal expansion in areas of the surgical instrument where any components thereof may be longitudinally displaced during operation. As best illustrated in FIGS. 12-13, scissoring portions 7330 include a first group of linkages 7332*a* associated with a first electrical path and a second group of linkages 7332*b* associated with a second electrical path. Each of the linkages 7332*a* and 7332*b* includes a wire portion 7333 terminated at each end by circular contacts 7334 for providing a conduction path along the length of a linkage linkable to an adjacent linkage. Additionally, the wire portions 7333 are covered with insulating material 7335 to avoid shorting between the first and second electrical paths when overlapping as shown in FIG. 12. Rivets or pins 7336 join conductive elements of a given group together to maintain electrical continuity along the length of the scissoring portion via circular contacts 7337. The mechanical portion of the linkages 7332*a* and 7332*b* comprise a high resiliency polymeric material to withstand any bending forces without fracturing and/or undergoing plastic deformation while maintaining an ability to longitudinally expand. Furthermore, one or more of the linkages 7332*a* and/or 7332*b* may be molded with a curved length and/or width to traverse a bend if necessary.

Various embodiments described herein are described in the context of staples removably stored within staple cartridges for use with surgical stapling instruments. In some circumstances, staples can include wires which are deformed when they contact an anvil of the surgical stapler. Such wires can be comprised of metal, such as stainless steel, for example, and/or any other suitable material. Such embodiments, and the teachings thereof, can be applied to embodiments which include fasteners removably stored with fastener cartridges for use with any suitable fastening instrument.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Pat. No. 8,733,613, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. U.S. Pat. No. 8,393,514, entitled SELECTIVELY ORIENTABLE IMPLANTABLE FASTENER CARTRIDGE, which issued on Mar. 12, 2013, is also hereby incorporated by reference in its entirety. One skilled in the art will recognize that the herein described components (e.g., operations), devices, objects, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference numbers included in the appended claims are used to reference exemplary embodiments/elements described in the present disclosure.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Various aspects of the subject matter described herein are set out in the following numbered examples:

Example 1—A surgical instrument (7000) comprising a shaft (7100), a multi-axis articulation joint assembly (7200) defining a cavity therein, and a wiring assembly (7300) disposed within the shaft and the multi-axis articulation joint assembly. The multi-axis articulation joint assembly comprises a proximal end (7201), a distal end (7202), a first articulation joint (7220) disposed between the proximal end and the distal end and a second articulation joint (7230) distal to the first articulation joint. The first articulation joint is configured to move in a first articulation plane, and the second articulation joint is configured to move in a second articulation plane transverse to the first articulation plane. The wiring assembly comprises a wiring harness (7310) extending through the cavity of the articulation joint assembly. The wiring harness has a thickness and a width greater than the thickness. The wiring harness comprises a proximal flat portion (7312) that spans the first articulation joint in a non-articulated state, a distal flat portion (7316) that spans the second articulation joint in the non-articulated state and a preset twist (7314) between the proximal flat portion and the distal flat portion. The preset twist biases the distal flat portion into a different orientation than the proximal flat portion, in the non-articulated state.

Example 2—The surgical instrument of Example 1, further comprising a retainer (7103) nested in the shaft, the retainer comprising a channel (7104) defined in an outer surface (7106) of the retainer, wherein the channel is to guide the wiring assembly toward the multi-axis articulation joint assembly.

Example 3—The surgical instrument of Examples 1 or 2, wherein the preset twist (7314) spans a longitudinal distance between the first articulation joint (7220) and the second articulation joint (7230).

Example 4—The surgical instrument of any one of Examples 1-3, wherein the wiring harness (7310) comprises a plurality of conductors (7320), a plurality of layers, or any combination thereof.

Example 5—The surgical instrument of Example 4, wherein the plurality of conductors (7320) are arranged in the plurality of layers to minimize electromagnetic interference.

Example 6—The surgical instrument of any one of Examples 1-5, wherein the width of the wiring harness (7310) at the proximal flat portion (7312) extends along a first bending plane intersecting the first articulation plane and the width of the wiring harness at the distal flat portion (7316) extends along a second bending plane intersecting the second articulation plane.

Example 7—The surgical instrument of Example 6, wherein the preset twist (7314) defines an angle corresponding to a rotational offset between the first articulation joint (7220) and the second articulation joint (7230).

Example 8—The surgical instrument of Examples 6 or 7, wherein the preset twist (7314) is maintained throughout a full range of motion of the multi-axis articulation joint assembly (7200).

Example 9—The surgical instrument of any one of Examples 6-8, wherein the preset twist (7314) is integrated into the wiring harness (7310) prior to assembling the surgical instrument.

Example 10—The surgical instrument of any one of Examples 6-9, wherein the proximal flat portion (7312) comprises a first orientation in the non-articulated state such that, in the articulated state, a first bend radius of the proximal flat portion extends through the thickness of the wiring harness (7310) at the proximal flat portion.

Example 11—The surgical instrument of Example 10, wherein the distal flat portion (7316) comprises a second orientation in the non-articulated state such that, in the articulated state, a second bend radius of the distal flat portion extends through the thickness of the wiring harness (7310) at the distal flat portion.

Example 12—The surgical instrument of Example 11, wherein the proximal flat portion (7312) is aligned with the first articulation joint such that the proximal flat portion bends without twisting in the articulated state, and wherein the distal flat portion (7316) is aligned with the second articulation joint such that the distal flat portion bends without twisting in the articulated state.

Example 13—The surgical instrument of any one of Examples 1-12, wherein the wiring harness (7310) remains unstretched during a full range of articulation of the articulation joint assembly (7200).

Example 14—The surgical instrument of Example 13, wherein a length of the wiring harness (7310) between the proximal end (7201) and the distal end (7202) remains unchanged during the full range of articulation of the articulation joint assembly (7200).

Example 15—The surgical instrument of any one of Examples 1-14, wherein, in the non-articulated state, the wiring harness (7310) in the cavity spans the first articulation joint (7220) and the second articulation joint (7230) without a separate biasing member.

Example 16—A surgical instrument comprising a shaft, a multi-axis articulation joint assembly defining a cavity therein, and a wiring assembly disposed within the shaft and the multi-axis articulation joint assembly. The multi-axis articulation joint assembly comprises a proximal end, a distal end, a first articulation joint disposed between the proximal end and the distal end and a second articulation joint distal to the first articulation joint. The first articulation joint is configured to move in a first articulation plane and the second articulation joint is configured to move in a second articulation plane transverse to the first articulation plane. The wiring assembly comprises a wiring harness extending through the cavity of the articulation joint assembly, wherein the wiring harness has a thickness and a width greater than the thickness. The wiring harness comprises a proximal flat portion that spans the first articulation joint in a non-articulated state, a distal flat portion that spans the second articulation joint in the non-articulated state and a preset twist between the proximal flat portion and the distal flat portion. The preset twist biases the distal flat portion into a different orientation than the proximal flat portion, in the non-articulated state.

Example 17—The surgical instrument of Example 16, further comprising a retainer nested in the shaft, the retainer comprising a channel defined in an outer surface of the retainer, wherein the channel is to guide the wiring assembly toward the multi-axis articulation joint assembly.

Example 18—The surgical instrument of Example 16, wherein the preset twist spans a longitudinal distance between the first articulation joint and the second articulation joint.

Example 19—The surgical instrument of Example 16, wherein the wiring harness comprises a plurality of conductors, a plurality of layers, or any combination thereof.

Example 20—The surgical instrument of Example 19, wherein the plurality of conductors are arranged in the plurality of layers to minimize electromagnetic interference.

Example 21—The surgical instrument of Example 16, wherein the width of the wiring harness at the proximal flat portion extends along a first bending plane intersecting the first articulation plane and the width of the wiring harness at the distal flat portion extends along a second bending plane intersecting the second articulation plane.

Example 22—The surgical instrument of Example 21, wherein the preset twist defines an angle corresponding to a rotational offset between the first articulation joint and the second articulation joint.

Example 23—The surgical instrument of Example 21, wherein the preset twist is maintained throughout a full range of motion of the multi-axis articulation joint assembly.

Example 24—The surgical instrument of Example 21, wherein the preset twist is integrated into the wiring harness prior to assembling the surgical instrument.

Example 25—The surgical instrument of Example 21, wherein the proximal flat portion comprises a first orientation in the non-articulated state such that, in the articulated state, a first bend radius of the proximal flat portion extends through the thickness of the wiring harness at the proximal flat portion.

Example 26—The surgical instrument of Example 25, wherein the distal flat portion comprises a second orientation in the non-articulated state such that, in the articulated state, a second bend radius of the distal flat portion extends through the thickness of the wiring harness at the distal flat portion.

Example 27—The surgical instrument of Example 26, wherein the proximal flat portion is aligned with the first articulation joint such that the proximal flat portion bends without twisting in the articulated state, and wherein the distal flat portion is aligned with the second articulation joint such that the distal flat portion bends without twisting in the articulated state.

Example 28—The surgical instrument of Example 16, wherein the wiring harness remains unstretched during a full range of articulation of the articulation joint assembly.

Example 29—The surgical instrument of Example 28, wherein a length of the wiring harness between the proximal end and the distal end remains unchanged during the full range of articulation of the articulation joint assembly.

Example 30—The surgical instrument of Example 16, wherein, in the non-articulated state, the wiring harness in the cavity spans the first articulation joint and the second articulation joint without a separate biasing member.

Example 31—An articulation joint assembly for a surgical instrument, the articulation joint assembly comprising a multi-axis articulation joint assembly defining a cavity therein and a wiring assembly disposed within the multi-axis articulation joint assembly. The multi-axis articulation joint assembly comprises a proximal end, a distal end, a first articulation joint disposed between the proximal end and the distal end and a second articulation joint distal to the first articulation joint, wherein the first articulation joint is configured to move in a first articulation plane, and wherein the second articulation joint is configured to move in a second articulation plane transverse to the first articulation plane. The wiring assembly comprises a wiring harness extending through the cavity of the articulation joint assembly, wherein the wiring harness has a thickness and a width greater than the thickness. The wiring harness comprises a proximal flat portion that spans the first articulation joint in a non-articulated state, a distal flat portion that spans the second articulation joint in the non-articulated state and a preset twist between the proximal flat portion and the distal flat portion, wherein the preset twist biases the distal flat portion into a different orientation than the proximal flat portion, in the non-articulated state.

Example 32—The articulation joint assembly of Example 31, wherein the preset twist spans a longitudinal distance between the first articulation joint and the second articulation joint.

Example 33—The articulation joint assembly of Example 31, wherein the width of the wiring harness at the proximal flat portion extends along a first bending plane intersecting the first articulation plane and the width of the wiring harness at the distal flat portion extends along a second bending plane intersecting the second articulation plane.

Example 34—The articulation joint assembly of Example 31, wherein the preset twist is integrated into the wiring harness prior to assembling the surgical instrument.

Example 35—The articulation joint assembly of Example 34, wherein the preset twist is molded into the wiring harness prior to assembling the surgical instrument.

While several configurations have been described, additional modifications are within the scope of the present disclosure, which is intended to cover any variations, uses, or adaptations of the disclosed configurations using its general principles.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. The instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term “control circuit” or “control system” may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein “control circuit” includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term “logic” may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms “component,” “system,” “module” and the like can refer to a computer-related entity, either hardware, a combination of hardware and software, software, or software in execution.

As used in any aspect herein, an “algorithm” refers to a self-consistent sequence of steps leading to a desired result, where a “step” refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as “processing,” “computing,” “calculating,” “determining,” “displaying,” or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in one aspect. Thus, appearances of the phrases "in one aspect," "in an aspect," "in an exemplification," and "in one exemplification" in various places throughout the specification are not necessarily all referring to the same aspect. The particular features, structures or characteristics may be combined in any suitable manner in various aspects.

It is worthy to note that any reference numbers included in the appended claims are used to reference exemplary embodiments/elements described in the present disclosure. Accordingly, any such reference numbers are not meant to limit the scope of the subject matter recited in the appended claims.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical instrument, the surgical instrument comprising:

a shaft;

a multi-axis articulation joint assembly defining a cavity therein, the multi-axis articulation joint assembly comprising:

a proximal end;

a distal end;

a first articulation joint disposed between the proximal end and the distal end; and a second articulation joint distal to the first articulation joint, wherein the first articulation joint is configured to move in a first articulation plane, and wherein the second articulation joint is configured to move in a second articulation plane transverse to the first articulation plane; and a wiring assembly disposed within the shaft and the multi-axis articulation joint assembly, the wiring assembly comprising a wiring harness extending through the cavity of the articulation joint assembly, wherein the wiring harness has a thickness and a width greater than the thickness, wherein the wiring harness comprises:

a proximal flat portion that spans the first articulation joint in a non-articulated state;

a distal flat portion that spans the second articulation joint in the non-articulated state; and a preset twist between the proximal flat portion and the distal flat portion, wherein the preset twist biases the distal flat portion into a different orientation than the proximal flat portion, in the non-articulated state.

2. The surgical instrument of claim 1, further comprising a retainer nested in the shaft, the retainer comprising a channel defined in an outer surface of the retainer, wherein the channel is to guide the wiring assembly toward the multi-axis articulation joint assembly.

3. The surgical instrument of claim 1, wherein the preset twist spans a longitudinal distance between the first articulation joint and the second articulation joint.

4. The surgical instrument of claim 1, wherein the wiring harness comprises a plurality of conductors, a plurality of layers, or any combination thereof.

5. The surgical instrument of claim 4, wherein the plurality of conductors are arranged in the plurality of layers to minimize electromagnetic interference.

6. The surgical instrument of claim 1, wherein the width of the wiring harness at the proximal flat portion extends along a first bending plane intersecting the first articulation plane and the width of the wiring harness at the distal flat portion extends along a second bending plane intersecting the second articulation plane.

7. The surgical instrument of claim 6, wherein the preset twist defines an angle corresponding to a rotational offset between the first articulation joint and the second articulation joint.

8. The surgical instrument of claim 6, wherein the preset twist is maintained throughout a full range of motion of the multi-axis articulation joint assembly.

9. The surgical instrument of claim 6, wherein the preset twist is integrated into the wiring harness prior to assembling the surgical instrument.

10. The surgical instrument of claim 6, wherein the proximal flat portion comprises a first orientation in the non-articulated state such that, in the articulated state, a first bend radius of the proximal flat portion extends through the thickness of the wiring harness at the proximal flat portion.

11. The surgical instrument of claim 10, wherein the distal flat portion comprises a second orientation in the non-articulated state such that, in the articulated state, a second bend radius of the distal flat portion extends through the thickness of the wiring harness at the distal flat portion.

12. The surgical instrument of claim 11, wherein the proximal flat portion is aligned with the first articulation joint such that the proximal flat portion bends without twisting in the articulated state, and wherein the distal flat portion is aligned with the second articulation joint such that the distal flat portion bends without twisting in the articulated state.

13. The surgical instrument of claim 1, wherein the wiring harness remains unstretched during a full range of articulation of the articulation joint assembly.

14. The surgical instrument of claim 13, wherein a length of the wiring harness between the proximal end and the distal end remains unchanged during the full range of articulation of the articulation joint assembly.

15. The surgical instrument of claim 1, wherein, in the non-articulated state, the wiring harness in the cavity spans the first articulation joint and the second articulation joint without a separate biasing member.

16. An articulation joint assembly for a surgical instrument, the articulation joint assembly comprising:

a multi-axis articulation joint assembly defining a cavity therein, the multi-axis articulation joint assembly comprising:

a proximal end;

a distal end;

a first articulation joint disposed between the proximal end and the distal end; and a second articulation joint distal to the first articulation joint, wherein the first articulation joint is configured to move in a first articulation plane, and wherein the second articulation joint is configured to move in a second articulation plane transverse to the first articulation plane; and a wiring assembly disposed within the multi-axis articulation joint assembly, the wiring assembly comprising a wiring harness extending through the cavity of the articulation joint assembly, wherein the wiring harness has a thickness and a width greater than the thickness, wherein the wiring harness comprises:

a proximal flat portion that spans the first articulation joint in a non-articulated state;

a distal flat portion that spans the second articulation joint in the non-articulated state; and a preset twist between the proximal flat portion and the distal flat portion, wherein the preset twist biases the distal flat portion into a different orientation than the proximal flat portion, in the non-articulated state.

17. The articulation joint assembly of claim 16, wherein the preset twist spans a longitudinal distance between the first articulation joint and the second articulation joint.

18. The articulation joint assembly of claim 16, wherein the width of the wiring harness at the proximal flat portion extends along a first bending plane intersecting the first articulation plane and the width of the wiring harness at the distal flat portion extends along a second bending plane intersecting the second articulation plane.

19. The articulation joint assembly of claim 16, wherein the preset twist is integrated into the wiring harness prior to assembling the surgical instrument.

20. The articulation joint assembly of claim 19, wherein the preset twist is molded into the wiring harness prior to assembling the surgical instrument.

* * * * *